United States Patent [19]

Baerts

[11] Patent Number: 5,415,052
[45] Date of Patent: May 16, 1995

[54] SAMPLER FOR MOLTEN METAL

[75] Inventor: Christiaan Baerts, Beringen-Paal, Belgium

[73] Assignee: Heraeus Electro-Nite International, N.V., Antwerp, Belgium

[21] Appl. No.: 192,469

[22] Filed: Feb. 7, 1994

[30] Foreign Application Priority Data

Feb. 9, 1993 [DE] Germany .................. 43 03 687.2

[51] Int. Cl.6 .................................................. G01N 1/12
[52] U.S. Cl. ...................... 73/864.55; 73/864.53; 73/DIG. 9; 73/864.51
[58] Field of Search ............... 73/864.51-864.59, 73/DIG. 9; 136/234; 266/99; 374/139, 140

[56] References Cited

U.S. PATENT DOCUMENTS

| 4,261,202 | 4/1981 | Kawamoto et al. | 374/139 |
|---|---|---|---|
| 4,528,849 | 7/1985 | Paschkis | 73/864.59 |
| 4,912,989 | 4/1990 | Cassidy | 73/866.5 |

FOREIGN PATENT DOCUMENTS

| 0107219 | 5/1984 | European Pat. Off. | |
|---|---|---|---|
| 3000201 | 7/1981 | Germany . | |
| 4101155 | 7/1991 | Germany . | |
| 1150149 | 4/1969 | United Kingdom . | |
| 2167326 | 5/1986 | United Kingdom . | |
| 429308 | 5/1974 | U.S.S.R. | 73/864.53 |
| 709973 | 1/1980 | U.S.S.R. | 73/864.53 |
| 1137373 | 1/1985 | U.S.S.R. | 73/DIG. 9 |
| 1354057 | 11/1987 | U.S.S.R. | 73/864.56 |

Primary Examiner—Hezron E. Williams
Assistant Examiner—Daniel S. Larkin
Attorney, Agent, or Firm—Panitch Schwarze Jacobs & Nadel

[57] ABSTRACT

A sampler for molten metal has a carrier body, in which a sample chamber and a prechamber, connected to the latter in a sealed manner via an inflow opening, are arranged one behind the other along the axis of the carrier body, the prechamber having an inlet duct passing through the carrier body. In order to provide a sampler that can be assembled easily and reliably, even with larger manufacturing tolerances, and that allows easy removal of the sample after sampling, the sample chamber is held axially against the prechamber by means of a spring element.

15 Claims, 1 Drawing Sheet

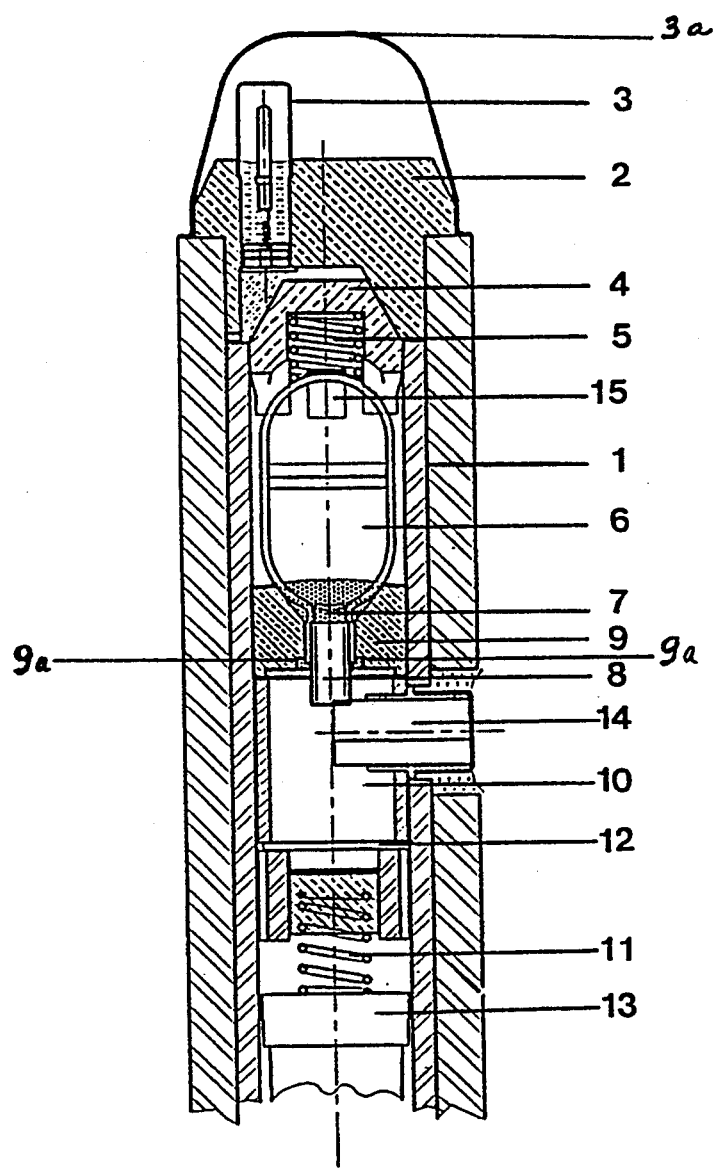

SAMPLER FOR MOLTEN METAL

FIELD OF THE INVENTION

The invention concerns a sampler for molten metal with a carrier body, in which a sample chamber and a prechamber, connected in a sealed manner to the latter via an inflow opening, are arranged one behind the other along the axis of the carrier body, the prechamber having an inlet duct passing through the carrier body.

BACKGROUND OF THE INVENTION

Samplers of this kind are known, for example, from DE 30 00 201, which describes a sampler with a carrier body in which is arranged a sample chamber that is connected to a prechamber via an inflow opening. The prechamber has an inlet duct for molten metal which passes through the lateral wall of the carrier body. The sample chamber and prechamber consist of separate housing parts that are fastened in the carrier body. Usually they are fastened by force fitting the parts into the carrier body, or by adhesively bonding them in with adhesive cement. High precision of the individual parts is needed in this context to ensure sealing. Thus, a relatively large expenditure of effort is needed in production of the individual sampler parts and in assembly.

A similar sampler is also known from GB 1,115,149, in which the sample chamber and prechamber have a shared lateral casing that is arranged in a carrier body. The two chambers are separated from one another by a separator member inserted in the shared casing. With this type of sampler, exact fixing of the separator member in the shared casing is necessary in order to produce a sample chamber of the desired size. Withdrawal of the sample, i.e., detachment of the sample chamber from the prechamber, is relatively complex with this arrangement, since first of all the shared casing must be destroyed.

The underlying object of the invention is therefore to provide a sampler that can be easily and reliably assembled even with larger manufacturing tolerances, and that allows easy removal of the sample after sampling.

SUMMARY OF THE INVENTION

According to the invention the aforesaid object is achieved by the sample chamber being held axially against the prechamber by means of a spring element. Such an arrangement guarantees that the sample chamber is always in zero-tolerance contact with the prechamber. The spring pressure compensates for the manufacturing tolerances which inevitably occur. Precise location of the sample chamber against the prechamber is ensured by the spring, and need not be undertaken manually. Assembly is therefore less time consuming, since there is no need for manual alignment of the sample chamber. After sampling, it is easy to remove the sample from the sampler, since the sample chamber is not permanently attached to the carrier body.

It is advantageous that the spring element is braced against a stop element fastened in the carrier body. This guarantees uncomplicated installation of the spring element, since the stop element ensures not only that the spring element seats firmly, but also that it can be located in an almost arbitrary fashion and with no alignment effort. It would also be possible, however, for the spring element to enclose the sample chamber and the prechamber from their sides facing away from one another, so that the two chambers are arranged between the pressure-exerting legs of the spring element.

Preferably, the stop element has a recess in which the spring element is retained in a centered manner. As a result, the spring element can be attached to the stop element before insertion into the carrier body, thus simplifying assembly. The spring element can be inserted into the recess and, optionally, adhesively bonded in said recess. As a result, it is fixed in the predetermined position during and after assembly.

Suitably, the sample chamber is arranged at the immersion end of the carrier body, and the spring element at the immersion end of the sample chamber. This allows easier removal of the sample chamber after sampling, since it is arranged at the end of the sampler. Usually samplers of the type described here are immersed from above into the vessel containing the molten metal. This immersion process often occurs automatically, i.e. the sampler is attached to a lifting and pivoting device. After sampling, the sampler is pivoted laterally out of the region of the vessel containing the molten metal and ejected, generally falling several meters. The impact from falling causes the sample chamber of a conventional sampler, which is still very hot, to deform, causing the sample to be no longer usable. When the spring element is arranged, as described above, at the front, it acts upon impact as a sort of buffer, which absorbs part of the impact energy and thereby prevents destruction of the sample chamber and thus of the sample.

It is advantageous for a quartz tube which projects into the prechamber to be arranged in the inflow opening, the quartz tube being fastened onto the sample chamber by means of a shaped member made of refractory material, and the shaped member being in contact with the side of the prechamber which faces the sample chamber. This shaped member can be made, for example, of conventional foundry sand. Suitably, it is fastened onto the sample chamber in force-fitting manner, for example by being pressed on, and the quartz tube is fastened to the carrier body by means of a refractory cement. On the one hand, this ensures that the sample chamber is in sealed contact with the prechamber, whereby the shaped member itself can form the boundary with the prechamber on the side facing the sample chamber. On the other hand, the shaped member protects the quartz tube which forms a duct for the admission of molten metal into the sample chamber. The quartz tube arranged between the sample chamber and the prechamber guarantees easy removal of the sample chamber, with the sample, from the carrier body.

Preferably, the spring element comprises a helical spring, especially a cylindrical helical spring. This allows a uniform axial transfer of force. It would also be possible to use conical helical springs or other spring elements, such as disk springs, leaf springs, spring washers, or spring columns.

It is advantageous to have a second spring element, which is held against a stop fastened in the carrier body, arranged at the boundary surface of the prechamber facing away from the immersion end. This simplifies alignment of the prechamber. During assembly, it is pressed into the carrier body against the spring element until the position of the opening provided for the inlet duct coincides with the position of the opening for the inlet duct located in the carrier element, and can be fastened for example by suitably attaching the opening in the carrier body to the opening in the prechamber.

This attachment can consist of a tube serving as the inlet duct.

It is useful, in the interest of simple production of the prechamber, for the boundary surface facing away from the immersion end to be configured as a cover plate. This cover plate is pressed by the second spring element in a sealed manner against the lateral walls of the prechamber. The force of the spring elements is advantageously 30N to 100N, preferably approximately 60N. This force is generally sufficient. Other, for example greater, forces are also possible, but as force increases, stronger bracing of the stops for the spring elements is also necessary.

The stop element arranged at the immersion end can usefully be configured as a measurement head to receive sensors, for example a thermocouple and/or an electrochemical sensor. This would make possible direct measurements of the molten metal simultaneously with sampling.

BRIEF DESCRIPTION OF THE DRAWING

The foregoing summary, as well as the following detailed description of a preferred embodiment of the invention, will be better understood when read in conjunction with the appended drawing. For the purpose of illustrating the invention, there is shown in the drawing an embodiment which is presently preferred. It should be understood, however, that the invention is not limited to the precise arrangements and instrumentalities shown. In the drawing:

The single FIGURE drawing shows the immersion end of a sampler in lengthwise section.

DETAILED DESCRIPTION OF THE PREFERRED EMBODIMENT

The sampler has a carrier body 1 that comprises two paperboard tubes, one inserted into the other. At its immersion end the carrier body 1 is sealed off with a measurement head 2 that has on the outside a sensor 3 and which is surrounded by a typical metal cap 3a. Inside the carrier body 1 the measurement head is configured as a stop element 4 that has a cylindrical helical spring 5 fastened in a recess. The helical spring 5 presses, at its end facing away from the measurement head, against a sample chamber 6 that has an inflow opening 7 on its end facing away from the immersion end of the sampler. Arranged on the inflow opening 7 is a quartz tube 8 that is attached to the sample chamber 6 in a sealed manner by means of a shaped member 9. The shaped member 9 is pressed onto the sample chamber 6 in the region of its inflow opening, and the quartz tube 8 is fastened onto the shaped member 9 by means of a refractory cement 9a. Under spring pressure, the shaped member 9 presses against the end of the prechamber 10 facing the sample chamber 6, thus creating a connection between the prechamber 10 and sample chamber 6 that is sealed off from the outside.

During assembly, the prechamber 10 is movably mounted by means of the second spring element 11, which is arranged between the cover plate 12 of the prechamber 10, and the stop 13 fastened in the carrier body 1. It is fixed in position by means of the inlet duct 14 which passes through openings in the carrier body 1 and in the side wall of the prechamber 10. The sample chamber 6, with the quartz tube 8 and shaped member 9, remains movable with respect to the helical spring 5. So that when the sampler falls to the ground after sampling, it is cushioned by the helical spring 5 and thus suffers no deformation. The risk of deformation would also exist, in particular, if the sample chamber 6 were designed as a flat sample chamber. In this case the flat sample chamber comprises two halves which can be parted parallel to the long axis of the sampler, and are held together by a clamp 15. After the cushioned impact with the ground, the sample chamber 6, and with it the sample, can be removed from the sampler undamaged.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. An immersion sampler useful for sampling molten metal comprising a hollow carrier body (1) having a longitudinal axis and an immersion end, a sample chamber (6) and a prechamber (10) arranged in the carrier body one behind the other along the axis of the carrier body, a molten metal inflow opening (7) connecting the sample chamber and prechamber in a sealed manner, the prechamber having an inlet duct passing through a wall of the carrier body, and a spring element (5) which holds the sample chamber (6) axially against the prechamber (10).

2. A sampler according to claim 1, wherein the spring element (5) is braced against a stop element (4) fastened in the carrier body (1).

3. A sampler according to claim 2, wherein the stop element (4) has a recess in which the spring element (5) is retained in a centered manner.

4. A sampler according to claim 2, wherein the stop element (4) is arranged at the immersion end and is configured as a measurement head (2) to receive sensors (3).

5. A sampler according to claim 1, wherein the sample chamber (6) is arranged at the immersion end of the carrier body (1), and the spring element (5) is arranged at the immersion end of the sample chamber (6).

6. A sampler according to claim 1, further comprising a quartz tube (8) arranged in the inflow opening (7) and projecting into the prechamber (10), the quartz tube (8) being fastened onto the sample chamber (6) by means of a shaped member (9) made of refractory material, and the shaped member (9) being in contact with an end of the prechamber (10) which faces the sample chamber (6).

7. A sampler according to claim 6, wherein the shaped member (9) contacts the sample chamber (6) in a force-fit manner, and the quartz tube (8) is fastened to the shaped member (9) by means of a refractory cement.

8. A sampler according to claim 1, wherein the spring element (5) comprises a helical spring.

9. A sampler according to claim 8, wherein the spring element (5) is a cylindrical helical spring.

10. A sampler according to claim 1, further comprising a second spring element (11), which is held against a stop (13) fastened in the carrier body (1), said second spring element being arranged at an end surface of the prechamber (10) facing away from the immersion end.

11. A sampler according to claim 10, wherein said end surface facing away from the immersion end is configured as a cover plate (12).

12. A sampler according to claim 10, wherein the force of the spring element (11) is 30N to 100N.

13. A sampler according to claim 12, wherein the force of the spring element (11) is approximately 60N.

14. A sampler according to claim 1, wherein the force of the spring element (5) is 30N to 100N.

15. A sampler according to claim 14, wherein the force of the spring element (5) is approximately 60N.

* * * * *